United States Patent [19]

Zipper

[11] 4,040,417
[45] Aug. 9, 1977

[54] INTRAUTERINE DEVICE

[75] Inventor: Jaime A. Zipper, Santiago, Chile

[73] Assignee: G. D. Searle & Co., Chicago, Ill.

[21] Appl. No.: 424,100

[22] Filed: Dec. 12, 1973

Related U.S. Application Data

[60] Division of Ser. No. 94,216, Dec. 1, 1970, Pat. No. 3,803,308, which is a continuation-in-part of Ser. No. 760,688, Sept. 18, 1968, Pat. No. 3,563,235.

[51] Int. Cl.$^2$ .............................................. A61F 5/46
[52] U.S. Cl. ...................................... 128/130; 128/260
[58] Field of Search ............... 128/130, 260, 268, 270; 424/140, 143, 145, DIG. 14

[56] References Cited

U.S. PATENT DOCUMENTS

| 3,184,376 | 5/1965 | Degoli | 424/145 |
| 3,533,406 | 10/1970 | Tatum | 128/130 |
| 3,576,186 | 4/1971 | Robinson | 128/130 |
| 3,683,906 | 8/1972 | Robinson | 128/130 |

OTHER PUBLICATIONS

Tatum, H. J.: Am. J. Obstet. Gynecol. 112 : 1014 and 1022, 1972.
White, I. G.: Aust. J. Exp. Biol. 33 : 359, 1955.
Saito, S., Bush, I. M., Willet, F. and Whitmore, J.: Fertil. Steril. 18 : 517, 1967.
Loewit, K.: Contraception 3: 219, 1971.
Himes, *Medical History of Contraception;* Gamut Press, Inc., New York, 1963; pp. 227, 228 and 231.

Primary Examiner—Lawrence W. Trapp
Attorney, Agent, or Firm—John A. Dhuey

[57] ABSTRACT

An intrauterine device including a contraceptively effective amount of non-toxic copper or zinc compound. The device is adapted to be inserted into the uterine cavity for a prolonged period of time.

3 Claims, No Drawings

INTRAUTERINE DEVICE

This application is a division of application Ser. No. 94,216, filed Dec. 1, 1970, and now U.S. Pat. No. 3,803,308, which is a continuation-in-part of application Ser. No. 760,688, filed Sept. 18, 1968, and now U.S. Pat. No. 3,563,235.

The present invention relates to a method for contraception, and relates in particular to a contraceptive method employing compounds of copper and zinc present in the uterus.

During the past several years, research in new contraceptive methods has been directed toward finding agents which will prevent fertility by a local action, rather than by the systemic action of agents taken orally or injected into the body. The advantage of locally acting agents, such as devices placed into the uterus, is that they produce no side effects, or few side effects, and do not interfere with the endocrine functions of the body as may happen with systemically acting agents like the steroid hormones (i.e. birth control pills.)

In view of the disadvantages of conventional hormonal birth control pills, inert intrauterine contraceptive devices were introduced for fetility control. It was found, however, that the intrauterine contraceptive devices which were already available and were being manufactured commercially, are not as effective as conventional oral administration of hormones. Considerable effort has since been directed toward improving the efficacy of intrauterine contraceptive devices.

The aforementioned patent application reports the discovery that the presence of elemental copper or zinc in the uterine cavity is highly effective in preventing conception. Thus, for example, a highly effective contraceptive method involves implanting elemental copper or zinc within the uterine cavity on a carrier. The carrier is suitably of an inert material such as plastic and may have any of a variety of forms including a single or multiple loop, spiral, cross, or various sinuous shapes. The metal is conveniently joined to the carrier in the form of a wire wound around a portion of the carrier.

According to the present invention, it has now been found that compounds of copper and zinc, such as the oxides (including the peroxides thereunder) or non-toxic copper or zinc salts, are highly effective in preventing pregnancy when introduced into the uterine cavity. The compounds can be used to prevent pregnancy in pets, such as dogs or cats, or in useful farm animals such as cattle and sheep. The present invention is of particular interest with reference to animals such as the cow or sheep, in which species the insertion of any device into the uterus is difficult because of the anatomical structure of the cervix. Yet it is of great importance to prevent pregnancy in such animals, especially when large herds are kept for fattening. Since pregnant animals may not be slaughtered, all pregnant animals from such herds have first to be treated to cause abortion. In addition to the costs thus incurred, the market value of such animals is usually lower.

To provide an antifertility effect one or more copper or zinc compounds are deposited into the uterine cavity either as solids or in a suspension or solution, for example by instillation. Generally solid or suspended material is used if a longer acting preparation is desired. A mechanical carrier may be used to prevent expulsion of the material from the uterine cavity where appropriate, or the solids or suspension may be introduced directly into the uterus, as in cattle or sheep. For example, such a carrier may consist of a perforated tube of a suitable length and diameter provided with small hooks or springs to hold the tube inside the uterus. The tube may also have various shapes resembling the commonly used intrauterine devices. Stainles steel, gold and other noble metals, inert polymeric materials (polyethylene, polypropylene, dimethylpolysiloxane, and the like), porous silicates, cellulose, or other inert materials may be used as materials for making such carriers. If desired, the solid material may be incorporated into the carrier, e.g. into a polymeric material and the resultant mixture formed into the desired shape.

Alternatively, solutions of copper or zinc compounds may be introduced into the uterus. Again, if desired, concentrated solutions of such salts may be enclosed in hollow carriers of various shapes to allow the active principle to diffuse slowly into the uterine cavity. Such hollow carriers can be made from inert porous materials having pores of sufficient size to allow diffusion. Various polymeric materials such as acetyl-cellulose, other hydrophilic polymers, porous silicates, and the like can be used to fabricate the carriers. Alternatively, the copper or zinc compounds may be adsorbed onto or bound to organic carriers such as gelatin, collagen and the like.

Any physiologically acceptable liquid may be used as a solvent or suspending agent, including water, saline solution, alcohol, ethylene glycol, and the like, or mixtures thereof.

In accordance with the present invention, copper or zinc compounds useful in preventing fertility include the non-toxic soluble and slightly soluble salts of inorganic and organic acids, such as copper sulfate, zinc sulfate, zinc chloride, zinc permanganate, copper acetate, copper gluconate, zinc oleate, or the like.. Also suitable are the oxides (including the peroxides) as, for example, copper oxide, zinc oxide, or zinc peroxide.

In general, the amount of copper or zinc compound inserted into the uterus is such as will provide from about 0.002 mg to 2 mg of soluble copper or zinc per day, preferably between about 0.01 to 0.1 mg daily. This can be achieved by controlling the crystal size of solids or the concentration of soluble or slightly soluble compounds in suspensions or solutions thereof.

A better understanding of the present invention will be had by referring to the following specific Examples, given by way of illustration.

EXAMPLE 1

The contraceptive properties of copper were determined in experimental animals in the following manner.

Adult female rats (4 per group) were selected in proestrus and caged with proven male breeder rats overnight. The presence of sperm in the vaginal lavage was considered evidence of pregnancy (day 1). On day 3 of pregnancy, the test substance was injected directly into the lumen of the left uterine horn; the right uterine horn was injected with an equal volume of 0.85% saline solution as a control. The volume of injected solution was 0.1 ml per horn. The rats were sacrificed and the numbers of implantations noted on day 10 of pregnancy.

The results are given below:

| Treatment | Average Body Weight (gm) | | Average No. of Implantations | |
|---|---|---|---|---|
| | Initial | Final | Left Treated horn | Right Control horn |
| Copper Sulfate (1% solution in saline) | 241 | 253 | 0 | 4.8 |
| No. rats implanted/No. rats | | | 0/4 | 4/4 |
| Copper Sulfate (5% solution in saline) | 242 | 255 | 0 | 4.0 |
| No. rats implanted/No. rats | | | 0/4 | 3/4 |

Thus, an instillation of even 0.1 ml of 1% copper sulfate solution was sufficient to prevent pregnancy. Alternatively, solutions of other copper salts, such as the acetate, can be employed.

When injected subcutaneously, dilute aqueous solutions of copper sulfate have no observable effect on the number of implantations in mated female rats.

EXAMPLE 2

The above experiment was repeated except that copper oxice (Cu O) suspended in 0.1 ml of 0.85% saline solution was injected into the uterine lumen at a point about 2 - 4 mm below the tubo-utero junction. Autopsy was on day 8 of pregnancy. Results:

| Results: Cu 0 | Average No. of implants | |
|---|---|---|
| μg | Right (Cu 0) | Left (control) |
| 150 | 4.3 | 6.3 |
| 300 | 3.0 | 6.4 |

Thus, the presence of copper oxide in the right uterine horn significantly decreased fertility in rats, as is apparent from the decreased number of viable implants.

EXAMPLE 3

Thirteen female rats were mated. After the appearance of sperm (day 1), 0.1 ml of a $10^{-2}$ M $CuSO_4$ solution was instilled into the right uterine horn of each animal at different times after pregnancy. The left horn was left untreated as a control. The number of implantations in each horn was determined, as shown below:

| IMPLANTATIONS | | |
|---|---|---|
| Days between instillation and sperm appearance | Right uterine horn | Left uterine horn (control) |
| 3 | 2 abortions | 4 |
| 4 | 1 abortion | 5 |
| 4 | 0 | 5 |
| 4 | 0 | 4 |
| 5 | 2     1 abortion | 5 |
| 7 | 5 | 1 |
| 9 | 7 | 2 |
| 11 | 0 | 6 |
| 13 | 0 | 0 |
| 13 | 4 | 1 |
| 14 | 0 | 3 |
| 20 | 0 | 1 |
| 25 | 0 | 3 |
| Average | 1.3     (0.3 abortions) | 3.0 |

EXAMPLE 4

Ten female rats were mated. In the third day post coitus, 0.1 ml of a $10^{-1}$ M copper acetate solution was instilled into the right uterine horn of each animal. 0.1 ml of a $10^{-1}$ M solution of sodium acetate was instilled into the left uterine horn of each animal as a control. The number of implantations in each horn was determined, as shown below:

| IMPLANTATIONS | |
|---|---|
| Right Horn (Cu Ac$_2$) | Left Horn (Na Ac) |
| 0 | 3 |
| 0 | 4 |
| 0 | 2 |
| 0 | 3 |
| 0     1 abortion | 4 |
| 0 | 4 |
| 0 | 0 |
| 0 | 0 |
| 0 | 0 |
| 0 | 5 |
| Average   0 | Average   2.5 |

What is claimed is:

1. An intrauterine device adaptable to insertion in the uterine cavity and capable of being retained therein for a prolonged period of time, said device including a contraceptively effective amount of non-toxic copper or zinc compound.

2. A device as in claim 1 wherein said compound is a copper oxide or a non-toxic copper salt.

3. A device as in claim 2 wherein said oxide or salt is present in the uterus in an amount providing from about 2 μg to about 2 mg of soluble copper per day.

* * * * *